United States Patent [19]

Ho et al.

[11] Patent Number: 5,461,162
[45] Date of Patent: Oct. 24, 1995

[54] PROCESS OF SYNTHESIZING N-ACYL AUXILIARIES

[75] Inventors: Guo-Jie Ho, Rahway; David J. Mathre, Skillman, both of N.J.

[73] Assignee: Merck & Co., Inc., Rahway, N.J.

[21] Appl. No.: 281,394

[22] Filed: Jul. 27, 1994

[51] Int. Cl.$^6$ .............. C07D 277/04; C07D 263/06; C07D 275/06; C07D 263/58
[52] U.S. Cl. .............. 548/188; 548/150; 548/171; 548/172; 548/221; 548/230
[58] Field of Search ............ 564/144; 548/230, 548/188, 150, 171, 172, 221

OTHER PUBLICATIONS

Kano, S. et al., J. of Org. Chem, 54 (3), pp. 513–515 (1989).
Ishizuka, T., et al., Tetrahedron, 49 (9), pp. 1841–1852 (1993).
Thaler, A. et al., Helv. Chim. Acta, 74, pp. 617–627 (1991).
Yamamoto, Y., et al., J. Org. Chem., 56, pp. 1112–1119 (1991).
J. Chem. Soc., Chem. Commun., 1992 pp. 1673–1674, by A. Ghosh, et al.
J. Org. Chem., vol. 55, No. 15 (1990) pp. 4585–4595, by D. Curran, et al.
J, Am. Chem. Soc., vol. 112, No. 7 (1990), pp. 2767–2772, by Oppolzer, et al.
J. Am. Chem. Soc. vol. 110, No. 25 (1988), pp. 8477–8482, by F. Davis, et al.
Liebigs Ann. Chem. (1989) pp. 739–750, by P. Binger, et al.
J. AM. Chem. Soc. (1982), 104, pp. 1737–1739, by E. Evans, et al.
Pure & Appl. Chem., vol. 62, No. 7, pp. 1241–1250 (1990), by W. Oppolzer.
J. Am. Chem. Soc., vol. 103, No. 8 (1981), pp. 2127–2129, by D. Evans, et al.
J. Am. Chem. Soc., vol. 106, No. 4 (1984), pp. 1154–1156, by D. Evans, et al.
Synthesis, Jun. 1992, pp. 582–586, by C. Thom, et al.
Synthesis in the Quinolizidine Series, Mar. 1949, vol. 71, pp. 879–886, by V. Boekelheide, et al.
Helvetica Chimica Acta, vol. 67 (1984), pp. 1397–1401, by W. Oppolzer, et al.
Helvetica Chimica Acta, vol. 70 (1987) pp. 1666–1675, by W. Oppolzer, et al.
Tetrahedron, vol. 43, No. 9 (1987), pp. 1969–2004, by W. Oppolzer.

*Primary Examiner*—Johann Richter
*Assistant Examiner*—Laura Cross
*Attorney, Agent, or Firm*—Richard C. Billups; Daniel Mark R.

[57] ABSTRACT

A process of synthesizing N-acyl auxiliary compounds is disclosed. A compound of the formula:

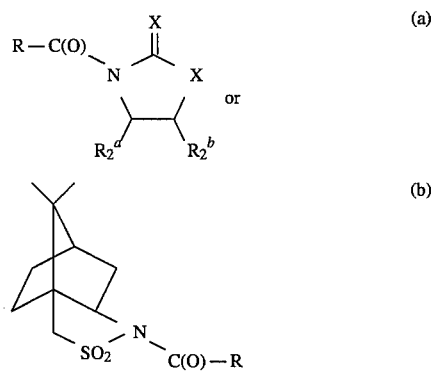

is reacted with an anhydride in the presence of a lithium salt and an amine base to produce the N-acylated auxiliary.

9 Claims, No Drawings

PROCESS OF SYNTHESIZING N-ACYL AUXILIARIES

BACKGROUND OF THE INVENTION

Chiral auxiliaries have been extensively used in asymmetric syntheses. Traditionally, the N-acyl 2-oxazolidinones have been synthesized by lithiating the oxazolidinone with n-butyl lithium at −78° C., followed by acylating with an acyl chloride. N-acyl sultams have been synthesized by deprotonation with NaH followed by N-acylation with an acyl chloride. Also, two step procedures have been used to convert the oxazolidinone or sultam to the trimethylsilyl derivative, followed by reaction with excess acyl chloride in refluxing toluene. Neither of these synthesis schemes is particularly useful when the acyl side chain contains substituent groups that are reactive. Also, it takes an inordinately long time for the reaction to run to completion. The present invention overcomes the disadvantages in these processes.

SUMMARY OF THE INVENTION

A process of synthesizing an N-acyl auxiliary compound of the formula:

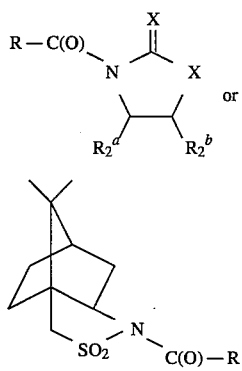

is disclosed.

Each X independently represents O or S. R represents a member selected from the group consisting of:

(a) $C_{1-6}$ alkyl, $C_{2-6}$ alkenyl or $C_{2-6}$ alkynyl;

(b) $C_{1-6}$ alkyl, $C_{2-6}$ alkenyl or $C_{2-6}$ alkynyl substituted with from 1–3 groups selected from: —$NH_2$; —OH; —COOH, —COO($C_{1-3}$) alkyl, —O$C_{1-4}$ alkyl; —C(O)—$C_{1-4}$ alkyl; —NH($C_{1-6}$ alkyl); —NH($C_{2-6}$ alkenyl); —NH($C_{2-6}$ alkynyl); —N($C_{1-6}$ alkyl)$_2$; —N($C_{2-6}$ alkenyl)$_2$; —N($C_{2-6}$ alkynyl)$_2$; —OC(O)$NH_2$; —OC(O)NH$C_{1-4}$ alkyl; —OC(O)N($C_{1-4}$alkyl)$_2$; aryl; heteroaryl; $C_{3-8}$ cycloalkyl; heterocyclyl; halo; —NHC(O)O$C_{1-6}$ alkyl; N($C_{1-3}$ alkyl)C(O)O$C_{1-6}$ alkyl; aryl, heteroaryl, $C_{3-8}$ cycloalkyl or heterocyclyl, said aryl, heteroaryl, cycloalkyl or heterocyclyl being unsubstituted or substituted with from 1–3 groups selected from halo, hydroxy, $C_{1-3}$ alkyl, $C_{1-3}$ alkoxy, hydroxy-$C_{1-3}$ alkyl, amino, $C_{1-3}$ alkylamino, and di-$C_{1-3}$ alkylamino, and (c) aryl, heteroaryl, $C_{3-8}$ cycloalkyl or heterocyclyl, unsubstituted or substituted with from 1–3 groups selected from halo, hydroxy, $C_{1-3}$ alkoxy, hydroxy-$C_{1-3}$ alkyl, amino, $C_{1-3}$ alkylamino, and di-$C_{1-3}$ alkylamino.

Each $R^a$ and $R^b$ independently represents H, $C_{1-4}$ alkyl, phenyl or $C_{1-4}$ alkyl substituted with 1–3 phenyl groups, or one $R^a$ and one $R^b$ represent H and the other $R^a$ and $R^b$ are taken together and represent a $C_{3-5}$ alkylidene group, which is optionally substituted with 1–3 groups selected from $C_{1-4}$ alkyl and phenyl, said alkylidene group being optionally fused to a benzene ring.

A compound of the formula:

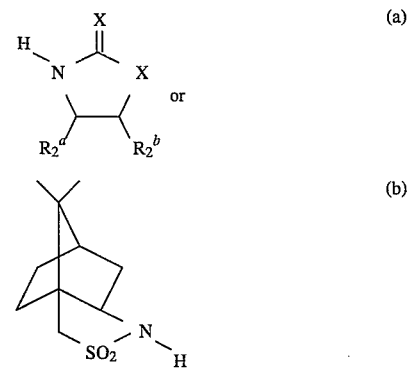

is reacted with an anhydride represented by the formula:

wherein each R is the same or different, and is as previously defined, in the presence of a lithium salt and an amine base to produce:

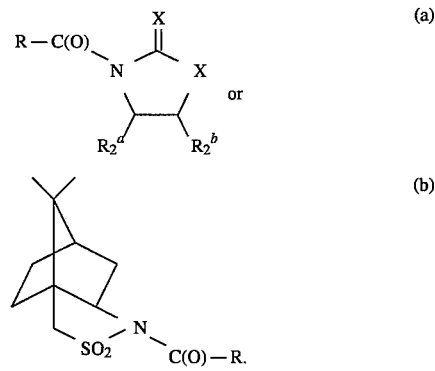

DETAILED DESCRIPTION OF THE INVENTION

As used herein, the following terms and definitions apply unless otherwise indicated.

The term "alkyl" refers to a monovalent alkane (hydrocarbon) derived radical containing from 1 to 6 carbon atoms unless otherwise defined. It may be straight or branched. Preferred alkyl groups include methyl, ethyl, propyl, isopropyl, butyl, or t-butyl. When substituted, alkyl groups may be substituted with up to four substituent groups, at any available point of attachment. When the alkyl group is said to be substituted with an alkyl group, this is used interchangeably with "branched alkyl group".

Alkylidene refers to a divalent group —$(CH_2)_{3-5}$— which typically forms a ring. In the compound

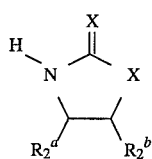

when one $R^a$ and $R^b$ represent H and the other $R^a$ and $R^b$ are taken in combination, the combination of $R^a$ and $R^b$ represents $C_{3-5}$ alkylidene. The following structures are applicable.

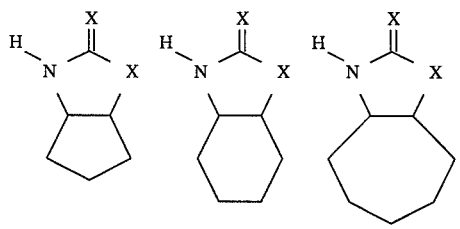

When the alkylidene is substituted, the substituent groups can be at any available point of attachment. All stereo configurations are intended at the two carbon atoms to which $R^a$ and $R^b$ are attached.

When the alkylidene group is fused to a phenyl ring, the fused phenyl ring can be across any available bond. The following are representative.

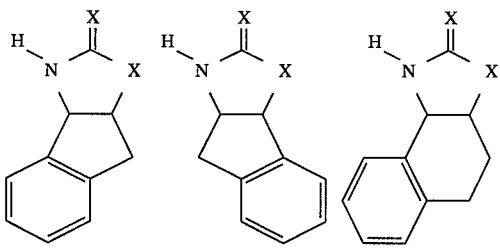

All such configurations are included in the invention.

The term "alkoxy" refers to a $C_{1-4}$ alkoxy radical: $-OC_{1-4}$ alkyl. The preferred alkoxy group is methoxy.

Cycloalkyl is a specie of alkyl containing from 3 to 15 carbon atoms, without alternating or resonating double bonds between carbon atoms. It may contain from 1 to 4 rings which are fused. The preferred cycloalkyl groups are cyclopentyl and cyclohexyl.

The term "alkenyl" refers to a hydrocarbon radical straight, branched or cyclic containing from 2 to 6 carbon atoms and at least one carbon to carbon double bond. Preferred alkenyl groups include ethenyl, propenyl, butenyl and cyclohexenyl.

The term "alkynyl" refers to a hydrocarbon radical straight or branched, containing from 2 to 6 carbon atoms and at least one carbon to carbon triple bond. Preferred alkynyl groups include ethynyl, propynyl and butynyl.

Aryl refers to aromatic rings e.g., phenyl, substituted phenyl and like groups, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl.

Aryl groups may likewise be substituted as defined. Preferred substituted aryls include phenyl and naphthyl.

The term "heteroatom" means O, S or N selected on an independent basis.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms are optionally replaced by a heteroatom selected from O or S, and in which from 1 to 3 additional carbon atoms are optionally replaced by nitrogen atoms, said heteroaryl group being optionally substituted as described herein.

Heteroaryl thus includes aromatic and partially aromatic groups which contain one or more heteroatoms. Examples of this type are pyrrole, pyridine, oxazole, thiazole and oxazine. Additional nitrogen atoms may be present together with the first nitrogen and oxygen or sulfur, giving, e.g., thiadiazole. Preferred heteroaryl groups are thiazolyl, imidazolyl, pyridyl and pyrrolyl.

The term "heterocycloalkyl" refers to a cycloalkyl group (nonaromatic) in which one of the carbon atoms in the ring is replaced by a heteroatom, and in which up to three additional carbon atoms may be replaced by heteroatoms. Preferred heterocycloalkyl groups include piperidinyl, pyrrolidinyl and tetrahydrofuranyl.

Halogen and "halo" refer to bromine, chlorine, fluorine and iodine.

The term "lithium salt" is used in the conventional sense, and refers to substantially non-basic lithium salts. Preferred salts are lithium chloride and bromide salts.

Amine bases as used herein refers to triethylamine, pyridine, diisopropylethylamine, lutidine, 1,8-diazobicyclo[5.4.0]undec-7-ene and 1,5-diazabicyclo[4.3.0]non-5-ene.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

Examples of suitable hydroxyl protecting groups which can be used in the syntheses described herein are: t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Preferred hydroxyl protecting groups are trimethylsilyl and triethylsilyl.

Examples of suitable carboxyl protecting groups are: benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl. A preferred carboxyl protecting group is p-nitrobenzyl.

In one aspect of the invention, the compound

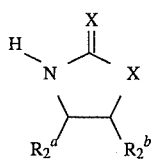

represents an oxazolidinone which contains at least one asymmetric center. The oxazolidinone is reacted with an anhydride. Examples of such oxazolidinones include the following:

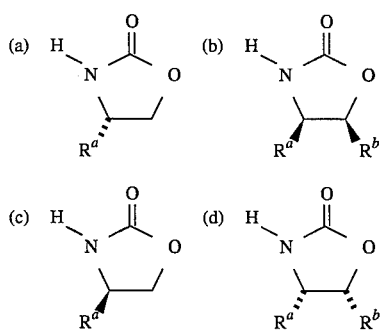

More particularly, this aspect of the invention includes reactions between anhydrides and oxazolidinone compounds wherein $R^a$ and $R^b$ are preferably $C_{1-4}$ alkyl, phenyl, or $C_{1-4}$ alkyl substituted with phenyl. Examples of these compounds include the following:

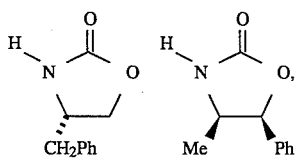

In another embodiment, one $R^a$ and one $R^b$ represent H and the other $R^a$ and $R^b$ taken together represent a $C_{3-5}$ alkylidene group. Examples include the following:

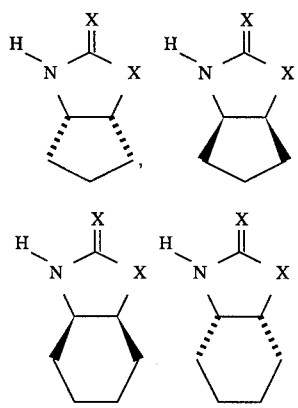

Likewise, the alkylidene group may be fused to a phenyl ring as exemplified below:

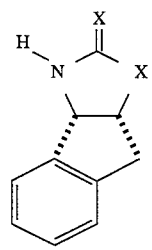

In a particular embodiment of the process, the oxazolidinone or sultam starting material is reacted with a mixed anhydride. Hence, the anhydride can be characterized as: $R^1$—C(O)—O—(O)—$R^2$, wherein $R^1$ and $R^2$ are different R groups. In a preferred embodiment, one of $R^1$ and $R^2$ is a pivalic acid residue, $(CH_3)_3C$—.

The oxazolidinone or sultam starting material is reacted with a mixed anhydride as described above in the presence of a lithium salt and an amine base. Lithium salts which can be used in this particular embodiment include the halide salts, e.g., LiCl and LiBr.

In another embodiment of the invention, one or both of the X variables represents S. Thus, the following compounds are included.

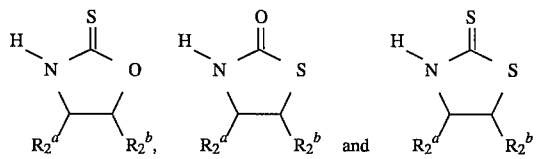

Amine bases which are suitable for use herein include triethylamine, pyridine, diisopropylethylamine, lutidine, 1,8-diazobicyclo[5.4.0]undec-7-ene and 1,5-diazabicyclo[4.3.0]non-5-ene. The preferred amine base is triethylamine.

In another embodiment of the invention, the anhydride is a symmetric anhydride which contains reactive groups. An example of this synthesis is acrylic anhydride, which can be reacted with any of the auxiliaries to perform the N-acylation.

Typically the reaction between the anhydride and the chiral auxiliary starting material can be completed in about 4 hours, at a temperature of about −20° C. to about 20° C.

The acylation reaction can be conducted in any appropriate organic solvent. The preferred solvent for use herein is tetrahydrofuran.

The invention is further described in connection with the following non-limiting examples.

PREPARATIVE EXAMPLE 1

PREPARATION OF ACRYLIC ANHYDRIDE

To a solution of acrylic acid (1.3 equiv.) and $Et_3N$ (2.5 equiv.) in THF was added acryloyl chloride (1.2 equiv.) at −20° C. A white solid was formed. The mixture was stirred at −20° C. for 1 hr to complete the reaction, producing acrylic anhydride 1a.

PREPARATIVE EXAMPLE 2

PREPARATION OF SYMMETRIC AND ASYMMETRIC ANHYDRIDES

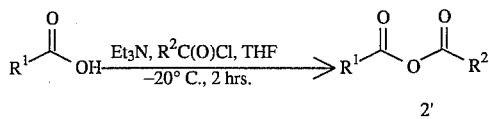

2'

Using the procedure set forth in Preparative Example 1, anhydrides can be prepared in accordance with the following table.

TABLE 2

| Cpd | R¹ | R² |
|---|---|---|
| 2a | N≡C—C₆H₄—(CH₂)₃— | (CH₃)₃C— |
| 3a | t-Boc-NH—(CH₂)₄— | (CH₃)₃C— |
| 4a | CH₃CH₂— | CH₃CH₂— |
| 5a | H₃C—CH=CH—CH₂— | H₃C—CH=CH—CH₂— |
| 6a | CH₂=C(CH₃)—CH₂— | CH₂=C(CH₃)—CH₂— |

EXAMPLE 1

(4R)-3-ACRYLOYL-4-PHENYLMETHYL-2-OXAZOLIDINONE

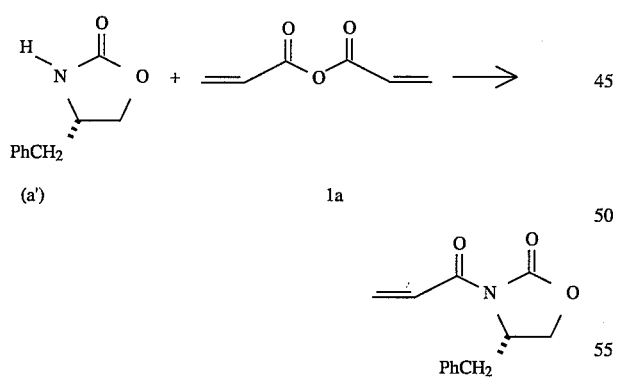

Acrylic anhydride was made in accordance with preparative example 1. The mixture was stirred for 1 hour. Lithium chloride (0.84 g, 20 mmol) was added followed by 4-phenylmethyloxazolidinone (a') (3.54 g). The mixture was allowed to warm to room temperature and was stirred for 4 hrs. The reaction was quenched with 0.2N HCl (2.0 equiv.). The THF was removed in vacuo and the residue was partitioned between ethyl acetate and 0.2N aqueous hydrochloric acid. The organic layer was subsequently washed with 0.2N HCl brine, 1M sodium bicarbonate (2×) and brine. The organic solution was then dried over sodium sulfate and filtered.

The ethyl acetate was removed in vacuo and the residue was dissolved in toluene. The toluene solution was filtered through a silica gel bed and the cake was washed with toluene. Concentration to dryness afforded the title compound 1 (4.15 g), which was crystallized by trituration with boiled hexane.

m.p. 72°–73° C. lit. m.p. 73°–74° C. [α]$_D$ (c)+110° (0.980). lit. [α]$_D$ (c)+71.9° (2.41). Note: [α]$_D$ (c) measured as dichloromethane solutions at 20° C. All lit [α]$_D$ (c) values reported as CHCl₃ solutions.

EXAMPLE 2

(4R)(5S) 3-PROPENOYL-4-METHYL-5-PHENYL-2-OXAZOLIDINONE

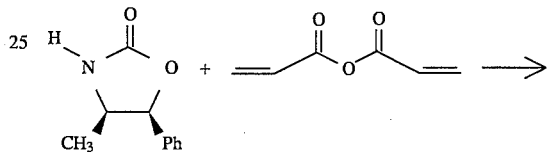

Acrylic anhydride produced in accordance with preparative example 1 was stirred for 1 hr at –20° C., combined with lithium chloride (1 equiv.) and (4R)(3S)-4-phenyl-3-methyloxazolidinone (0.885 g, 5.0 mmol.) was added as described in Example 1 above. The solvent is removed under vacuum. Concentration to dryness afforded the title compound 2 as an oil. The compound was further purified by flash chromatography on silica gel (1:3 ethyl acetate/hexane). (0.98 g).

[α]$_D$ (c)+20.5° (1.28). lit. [α]$_D$ (c)+29.0° (2.61).

EXAMPLE 3

(4R)-3-N-PROPENOYL-TETRAHYDROINDENO-2-OXAZOLIDINONE

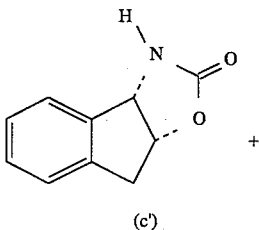

(c')

-continued

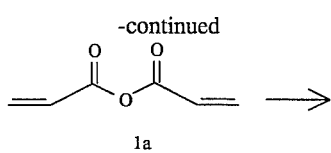

1a

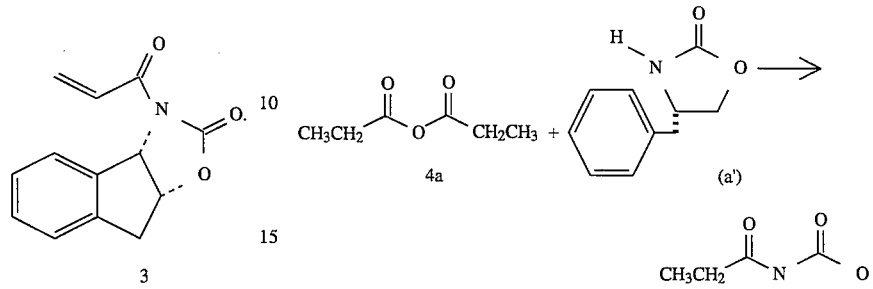

Using the procedure set forth in Example 2, the unsubstituted tetrahydroindenyl oxazolidinone (c') (0.876 g, 5.0 mmol.) was converted to the title compound 3 as a white crystalline solid (0.963 g).

mp 141°–142° C., [α]$_D$ (c)+406° (1.36). $^1$H NMR: δ7.68 (d, 1H, J=7 Hz), 7.50 (dd, 1H, J=10, 17 Hz) 7.30 (m, 3H), 6.64 (dd, 1H, J=2, 17 Hz), 6.60 (d, 1H, J=7 Hz), 5.93 (dd), 1H, J=2, 10 Hz), 5.33 (m, 1H), 3.40 (d, 2H, J=3.5 Hz).

EXAMPLE 4

(−)-N-PROPENOYLBORNANE-2, 10-SULTAM

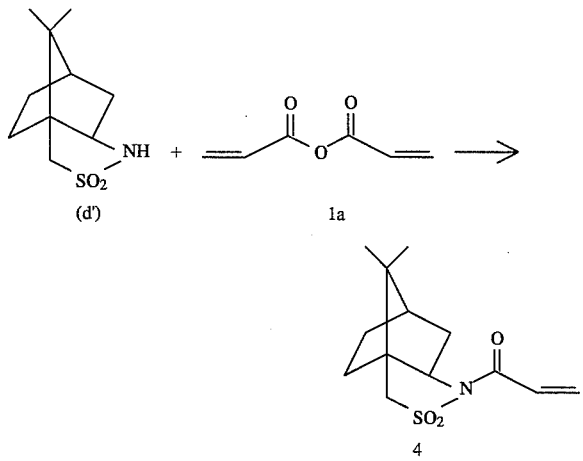

Acrylic anhydride 1a and bornane-2, 10-sultam (d') (1.72 g) are reacted in accordance with Example 2 set forth above. Crystallization of the crude product from toluene/hexane gave the title compound 4 as a whim crystalline solid (1.71 g). A second crop was obtained by evaporating the filtrate and triturating with boiling hexane. (0.215 g).

mp 184° C. (dec). lit. mp>170° C. [α]$_D$ (c)−98.5° (1.05). lit. [α]$_D$ (c)−100.9° (0.983).

EXAMPLE 5

(4R)-3-PROPIONYL-4-(PHENYLMETHYL)-2-OXAZOLIDINONE

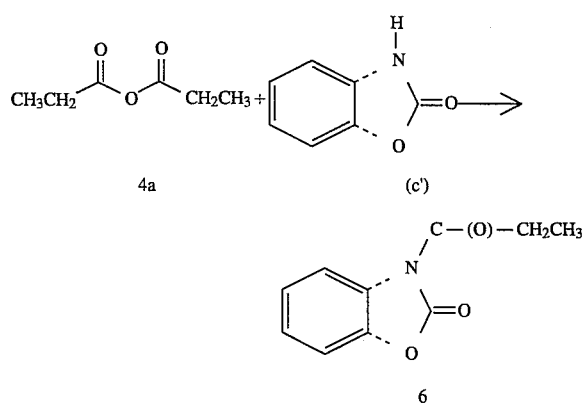

To a solution of 4-phenylmethyl-2-oxazolidinone (a') (0.887 g, 5.0 mmol), lithium chloride (1.0 equiv.) and triethylamine (1.3 equiv.) in THF (0.2M) was added propionic anhydride 4a (1.2 equiv.) at −20° C. The mixture was allowed to warm to room temperature and stirred for 4 hrs. THF was removed in vacuo and the residue was partitioned between EtOAc and 0.2N aqueous HCl. The organic layer was subsequently washed with brine, 1M NaHCO$_3$ and brine. The organic solution was dried over sodium sulfate and filtered. The ethyl acetate was removed in vacuo, and the residue was crystallized by trituration with boiling hexane producing the title compound 5 (1.09 g).

m.p. 44°–45° C. lit. m.p. 45°–46° C. [α]$_D$(c)+84.1° (1.02). lit [α]$_D$ (c)+80.7° (1.00).

EXAMPLE 6

N-PROPIONYL-TETRAHYDROINDENO-2-OXAZOLIDINONE

Substitute tetrahydroindeno-2-oxazolidinone (c') (0.876 g, 5.0 mmol) for 4-phenylmethyl-2-oxazolidinone (a') in the procedure set forth in Example 5, producing the title compound 6 as a white crystalline solid (1.06 g).

m.p. 128°–129° C. lit. m.p. 130° C. [α]$_D$ (c)+296° (1.00). lit [α]$_D$ (c)+268° (2.4).

¹H NMR: δ7.65 (d, 1H, J=8 Hz), 7.30 (m, 3H), 5.94 (d, 1 H, J=7 Hz), 5.37 (m, 1H), 3.38(d, 2H, J=3.5 Hz), 2.95 (q, 2H, J=7.3 Hz), 1.20 (t, 3H, J=7.3 Hz).

EXAMPLE 7

(−)-N-PROPIONYL-BORNANE-2,10-SULTAM

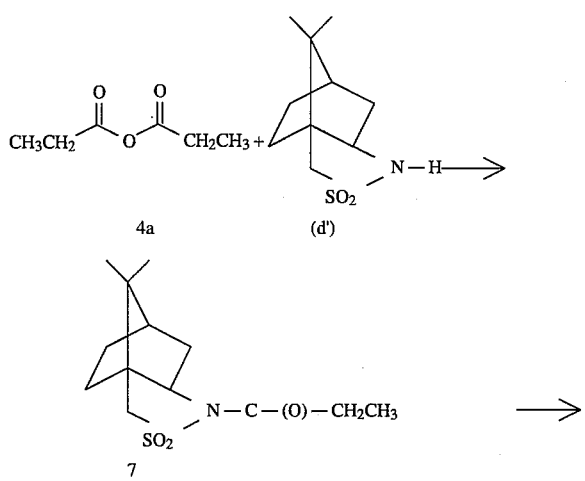

Substitute bornane-2,10-sultam (d') (1.08 g, 5.0 mmol) for 4-(phenylmethyl)-2-oxazolidinone in the procedure set forth in Example 5 to produce the title compound 7 as a white crystalline solid (1.29 g).

m.p. 151°–152° C. lit. m.p. 153°–154° C. [α]$_D$ (c)−113° (1.34). lit [α]$_D$ (c)−108.4° (2.65).

EXAMPLE 8

(4R)-3-((E)-2-BUTENOYL)-4-(PHENYLMETHYL)-2-OXAZOLIDINONE

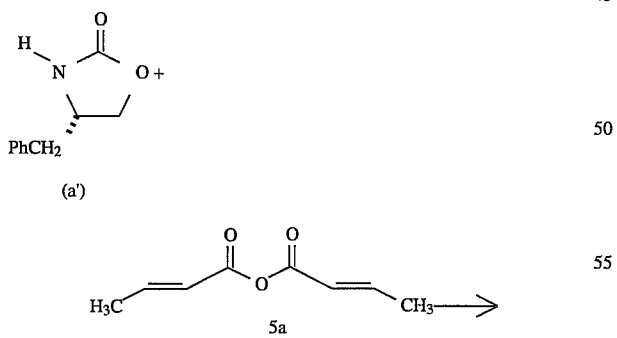

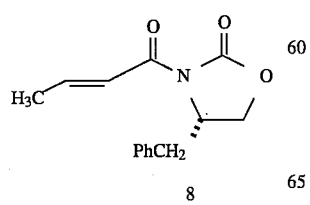

Substitute (E)-2-butenoic anhydride 5a for propionic anhydride in the process set forth in Example 5 above to produce the title compound 8 (1.08 g).

m.p. 84°–85° C. lit m.p. 85°–86° C. [α]$_D$ (c)+106° (1.07). lit [α]$_D$ (c)+94.6° (1.65).

EXAMPLE 9

(−)-N-((E)-2-BUTENOYL)-BORNANE-2,10-SULTAM

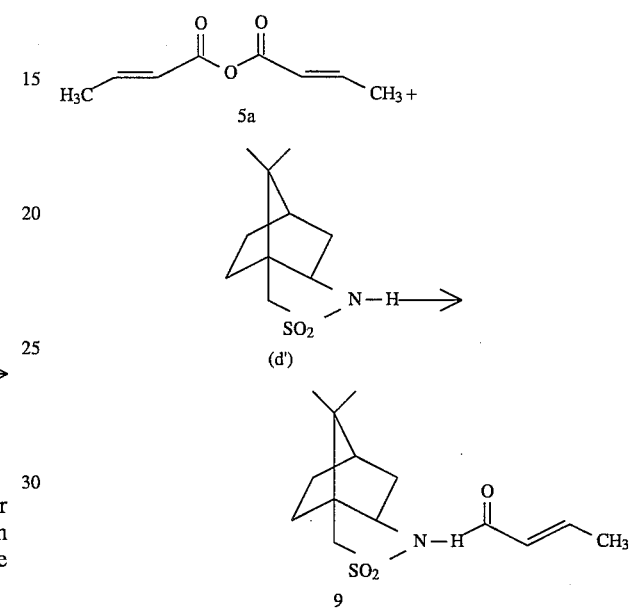

Substitute bornane-2,10-sultam (d') (1.08 g, 5.0 mmol) for 4-(phenylmethyl)-2-oxazolidinone in the procedure set forth in Example 8 to produce the title compound 9 as a white crystalline solid.(1.23 g).

m.p. 182°–183° C. lit. m.p. 186°–187° C. [α]$_D$ (c)−82.30° (1.15). lit [α]$_D$ (c)−99.5° (1.04).

EXAMPLE 10

(4R)(5S)-3-(2-METHYLPROPENOYL)-4-METHYL-5-PHENYL-2-OXAZOLIDINONE

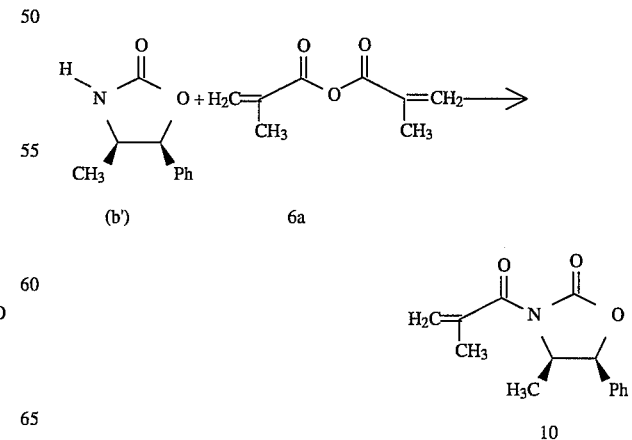

Substitute 2-methyl-2-propenoic anhydride 6a for propionic anhydride and 4-methyl-5-phenyl-2-oxazolidinone (b') (0.886 g, 5.0 mmol) for 4-(phenylmethyl)-2-oxazolidinone in the procedure set forth in Example 5 to produce the title compound 10. (1.10 g.).

m.p. 79°–80° C. lit. m.p. 80°–81° C. $[\alpha]_D$ (c)+35.3° (1.23). lit $[\alpha]_D$ (c)+36.8° (1.27).

EXAMPLE 11

(4R)-3-(4-(4'-PYRIDYL)-BUTANOYL)-4-PHENYLMETHYL)-2-OXAZOLIDINONE

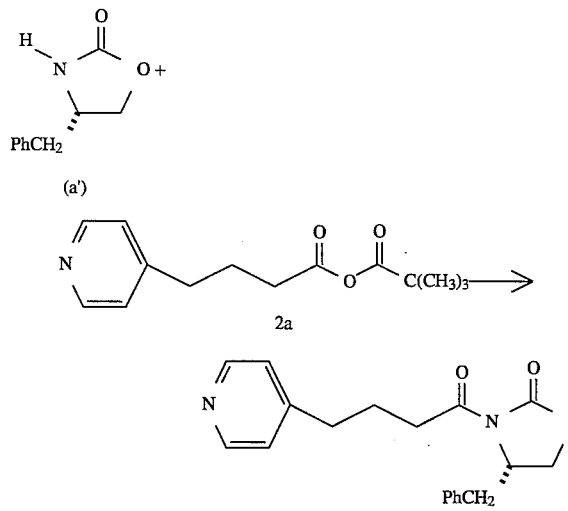

To a solution of 4-(4'-pyridyl)butanoyl pivalic anhydride 2a, and triethylamine (4.05 g, 40 mmol) in THF (120 mL) was added lithium chloride (0.47 g, 10 mmol), followed by 4-phenylmethyl-2-oxazolidinone (a') (1.77 g, 10 mmol). The mixture was warmed up to room temperature and further stirred for 4 hrs. THF was removed in vacuo. The residue was partitioned between ethyl acetate (80 mL) and water (40 mL). The organic layer was washed with 1M sodium bicarbonate (2×40 mL) and brine (40 mL). The solvent was evaporated in vacuo and an oil was obtained. The oil crystallized upon standing overnight to produce the title compound 11 (2.96 g).

mp: 73°–74° C. $[\alpha]_D$(c)+61.2° (1.15). $^1$H NMR: δ8.50 (d, 2H, J=5.9 Hz), 7.25 (m, 7H), 4.65 (m, 1H), 4.20 (m, 2H), 3.30 (dd, 1H, J=3.3, 13 Hz), 3.0 (m, 2H), 2.73 (m, 3H), 2.08 (m, 2H).

EXAMPLE 12

(4R, 5S)-3-(5-N-BOC AMINO-VALERYL)-4-METHYL-5-PHENYL-2-OXAZOLIDINONE

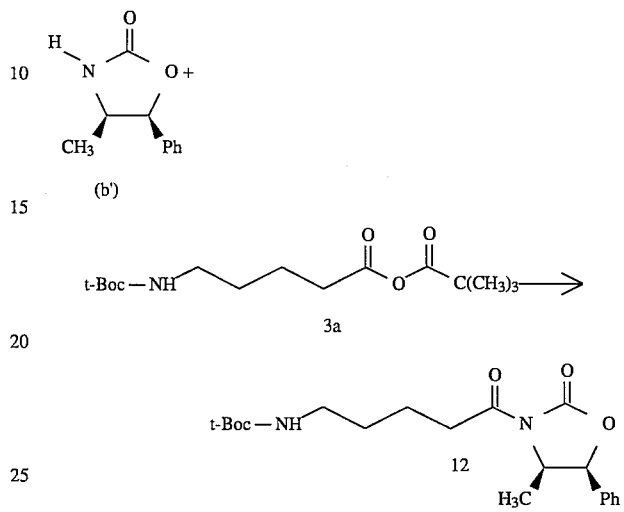

To a solution of 5-N-Boc amino valeroyl pivaloyl anhydride 3a and triethylamine (2.13 g, 21 mmol) in THF (50 mL) was added lithium chloride (0.39 g, 9.1 mmol) followed by 4-methyl-5-phenyl-2-oxazolidinone (b') (1.42 g, 8.0 mmol). The mixture was warmed to room temperature and further stirred for 4 hrs. THF was removed in vacuo and the residue was partitioned between ethyl acetate (50 mL) and 5% potassium hydrogen sulfate (30 mL). The organic layer was washed with potassium hydrogen sulfate (30 mL), brine (30 mL), 1M sodium bicarbonate (2×30 mL), and brine (30 mL). The ethyl acetate solution was dried over sodium sulfate and filtered. Evaporation of ethyl acetate gave the title compound 12 as an oil, which solidified upon standing (2.92 g).

m.p. 103°–104° C. $^1$H NMR: δ7.35 (m, 5H), 5.67 (d, 1H, J=13 Hz), 4.75 (m, 2H), 4.62 (br, 1H), 3.18 (m, 2H), 2.95 (m, 2H), 1.72 (m, 2H), 1.58 (m, 2H), 1.45 (s, 9H), 0.9 (d, 3H, J=8 Hz).

EXAMPLE 13

(–)-N-(2-METHYLPROPENOYL)-BORNANE-2,10-SULTAM

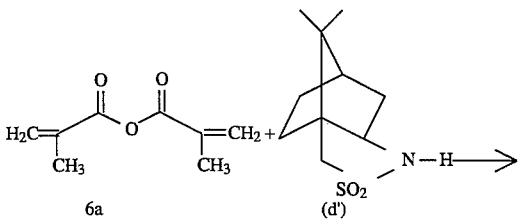

-continued

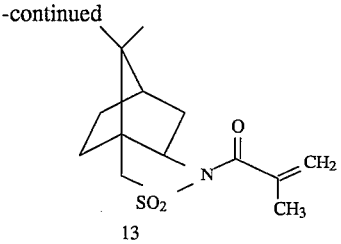

13

Substitute bornane-2,10-sultam for 4-methyl-5-phenyl-2-oxazolidinone (d') in the process set forth in Example 10 to produce the title compound 13 as a white crystalline solid (1.35 g).

m.p. 147°–148° C. $[\alpha]_D$ (c)–95.6° (1.23). lit $[\alpha]_D$ (c)+93° (1.00). $^1$H NMR: δ5.67 (m, 2H), 4.05 (m, 1H), 3.51 (d, 1H, J=14 Hz), 3.40 (d, 1H, J=14 Hz), 2.00 (s, 3H), 1.95 (m, 5H), 1.40 (m, 2H), 1.21 (s, 3H), 1.00 (s, 3H).

What is claimed is:

1. A process of synthesizing an N-acyl auxiliary compound of the formula:

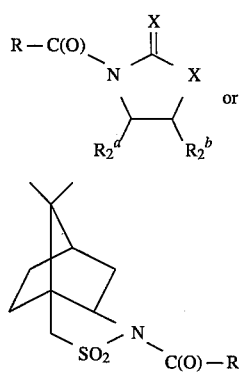

wherein:
  each X independently represents O or S;
  R represents a member selected from the group consisting of:
  (a) $C_{1-6}$ alkyl, $C_{2-6}$ alkenyl or $C_{2-6}$ alkynyl;
  (b) $C_{1-6}$ alkyl, $C_{2-6}$ alkenyl or $C_{2-6}$ alkynyl substituted with from 1–3 groups selected from: —$NH_2$; —OH; —COOH, —COO($C_{1-3}$) alkyl, —O$C_{1-4}$ alkyl; —C(O)—$C_{1-4}$ alkyl; —NH($C_{1-6}$ alkyl); —NH($C_{2-6}$ alkenyl); —NH($C_{2-6}$ alkynyl); —N($C_{1-6}$ alkyl)$_2$; —N($C_{2-6}$ alkenyl)$_2$; —N($C_{2-6}$ alkynyl) $_2$; —OC(O)$NH_2$; —OC(O)NH$C_{1-4}$ alkyl; —OC(O)N($C_{1-4}$ alkyl)$_2$; aryl; heteroaryl; $C_{3-8}$ cycloalkyl; heterocyclyl; halo; —NHC(O)O$C_{1-6}$ alkyl; N($C_{1-3}$ alkyl)C(O)O$C_{1-6}$ alkyl; aryl, heteroaryl, $C_{3-8}$ cycloalkyl or heterocyclyl group substituted with from 1–3 groups selected from halo, hydroxy, $C_{1-3}$ alkyl, $C_{1-3}$ alkoxy, hydroxy-$C_{1-3}$ alkyl, amino, $C_{1-3}$ alkylamino, and di-$C_{1-3}$ alkylamino, and
  (c) aryl, heteroaryl, $C_{3-8}$ cycloalkyl or heterocyclyl, unsubstituted or substituted with from 1–3 groups selected from halo, hydroxy, $C_{1-3}$ alkoxy, hydroxy-$C_{1-3}$ alkyl, amino, $C_{1-3}$ alkylamino, and di-$C_{1-3}$ alkylamino;
  each $R^a$ and $R^b$ independently represents H, $C_{1-4}$ alkyl, phenyl or $C_{1-4}$ alkyl substituted with 1–3 phenyl groups,
  or one $R^a$ and one $R^b$ represent H and the other $R^a$ and $R^b$ are taken together and represent a $C_{3-5}$ alkylidene group, which is optionally substituted with 1–3 groups selected from $C_{1-4}$ alkyl and phenyl, said alkylidene group being optionally fused to a benzene ring;

comprising:

reacting a compound of the formula:

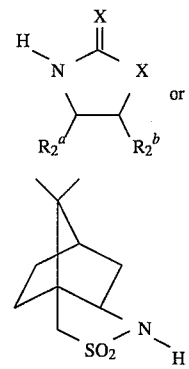

with an anhydride represented by the formula:

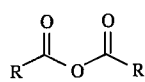

wherein each R group is the same or different and is as previously defined, in the presence of a lithium salt and an amine base to produce:

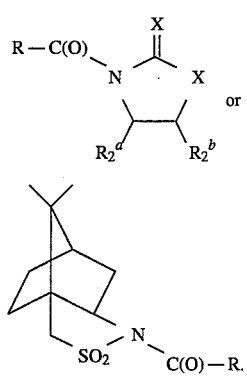

2. A process in accordance with claim 1 wherein a compound of the formula

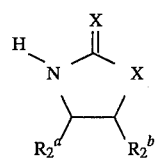

is reacted with an anhydride represented by the formula:

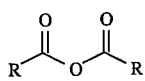

wherein R is as previously defined, in the presence of a lithium salt and an amine base to produce:

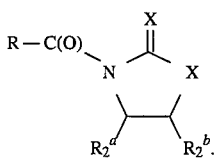

3. A process in accordance with claim 2 wherein the compound:

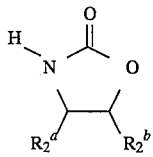

constitutes a member selected from the group consisting of:

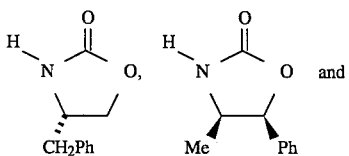

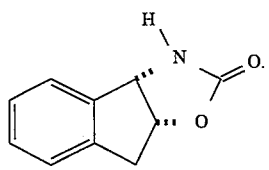

4. A process in accordance with claim 1 wherein a compound of the formula:

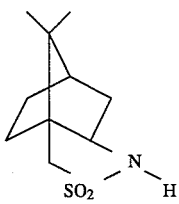

is reacted with an anhydride represented by the formula:

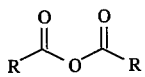

wherein R is as previously defined, in the presence of a lithium salt and an amine base to produce:

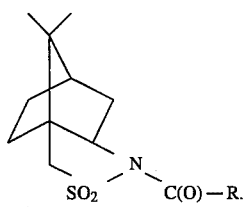

5. A process in accordance with claim 1 wherein a compound of the formula:

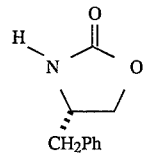

is reacted with an anhydride of the formula:

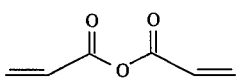

in the presence of LiCl and Et$_3$N to produce a compound of the formula:

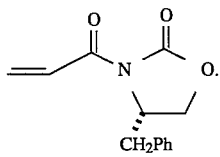

6. A process in accordance with claim 1 wherein a compound of the formula:

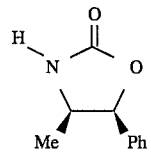

is reacted with an anhydride of the formula:

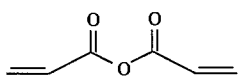

in the presence of LiCl and Et$_3$N to produce a compound of the formula:

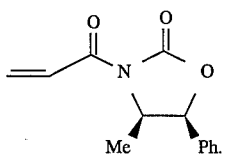

7. A process in accordance with claim 1 wherein a compound of the formula:

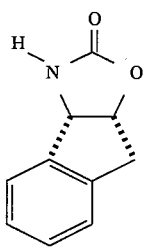

is reacted with an anhydride of the formula:

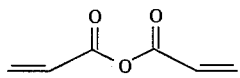

in the presence of LiCl and Et₃N to produce a compound of the formula:

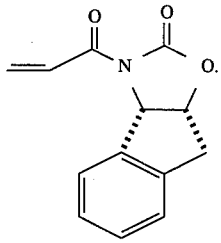

8. A process in accordance with claim 1 wherein a compound of the formula:

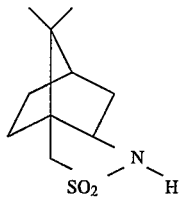

is reacted with an anhydride of the formula:

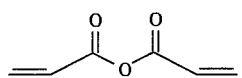

in the presence of LiCl and Et₃N to produce a compound of the formula:

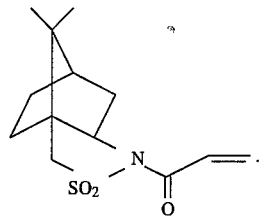

9. A process in accordance with claim 2 wherein the compound:

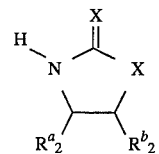

is selected from the group consisting of:

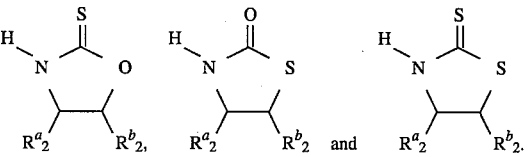

* * * * *